(12) United States Patent
Paxson et al.

(10) Patent No.: US 7,769,576 B2
(45) Date of Patent: Aug. 3, 2010

(54) METHOD AND APPARATUS FOR INTEGRATED MODELING, SIMULATION AND ANALYSIS OF CHEMICAL AND BIOLOGICAL SYSTEMS HAVING A SEQUENCE OF REACTIONS, EACH SIMULATED AT A REACTION TIME DETERMINED BASED ON REACTION KINETICS

(75) Inventors: Ricardo E. Paxson, Boston, MA (US); Joseph F. Hicklin, Upton, MA (US)

(73) Assignee: The MathWorks, Inc., Natick, MA (US)

( * ) Notice: Subject to any disclaimer, the term of this patent is extended or adjusted under 35 U.S.C. 154(b) by 1035 days.

(21) Appl. No.: 11/174,170

(22) Filed: Jun. 30, 2005

(65) Prior Publication Data

US 2007/0005317 A1  Jan. 4, 2007

(51) Int. Cl.
*G06G 7/58* (2006.01)
*G01N 33/48* (2006.01)

(52) U.S. Cl. .............................. 703/12; 702/11; 702/20; 703/6; 703/11

(58) Field of Classification Search ....................... None
See application file for complete search history.

(56) References Cited

FOREIGN PATENT DOCUMENTS

WO  WO-02/08839 A1  1/2002

WO  WO-2004/081862 A2  9/2004

OTHER PUBLICATIONS

Keener, J. and Sneyd, J., Mathematical Physiology, Springer, New York, 1998. (Only cover pages, table of contents and pp. 3-16 are herein provided.).*
Gillespie, Daniel T., "Exact Stochastic Simulation of Coupled Chemical Reactions," *The Journal of Physical Chemistry*, vol. 81 (25):2340-2361 (1977).
Invitation to Pay Additional Fees for Application No. PCT/US2006/026126, dated Dec. 21, 2006.
International Search Report for Application No. PCT/US2006/026126, dated Mar. 8, 2007.

* cited by examiner

*Primary Examiner*—Shubo (Joe) Zhou
(74) *Attorney, Agent, or Firm*—Lahive & Cockfield, LLP; Kevin J. Canning

(57) ABSTRACT

A system for modeling, simulating and analyzing chemical and biochemical reactions includes a modeling environment for constructing a model of a chemical or biochemical system comprising a plurality of chemical reactions. Each chemical reaction has a probability distribution associated therewith based on the kinetics of the particular chemical reaction. The probability distribution may be set by a user, determined automatically, or experimentally determined. The system also includes a simulation engine accepting as input said constructed model of the chemical or biochemical system and generating as output an expected result. The simulation engine calculates a reaction time for each chemical reaction based on the probability distribution associated with the particular chemical reaction. An analysis environment communicates with the simulation engine and displays the expected result.

32 Claims, 6 Drawing Sheets

Reaction Table

| Reaction | Kinetic Law | Parameter | Reversible |
|---|---|---|---|
| s70 + RNAP -> s70:RNAP | Mass Action | K | true |
| pg + s70:RNAP -> s70:RN... | Mass Action | K | true |
| s70:RNAP:pg -> mRNA_32 | Mass Action | K | true |
| mRNA_32 -> null | Mass Action | K | false |
| mRNA_32 -> s32 | Mass Action | K | true |
| s32 -> null | Mass Action | K | false |
| s32 + RNAP -> s32:RNAP | Mass Action | K | true |
| ph + s32:RNAP -> s32:RN... | Mass Action | K | true |
| s32:RNAP:ph -> mRNA_DnaK | Mass Action | K | true |
| mRNA_DnaK -> null | Mass Action | K | false |
| mRNA_DnaK -> DnaK | Mass Action | K | true |
| DnaK -> null | Mass Action | K | false |
| s32 + DnaK -> s32:DnaK | Mass Action | K | true |
| Punfolded + DnaK -> Punfo... | Mass Action | K | true |
| Punfolded:DnaK + Pfolded | Mass Action | K | true |
| Pfolded -> Punfolded | Mass Action | K | true |
| s32:RNAP:ph -> mRNA_FtsH | Mass Action | K | true |
| mRNA_FtsH -> null | Mass Action | K | false |
| mRNA_FtsH -> FtsH | Mass Action | K | true |
| FtsH -> null | Mass Action | K | false |
| s32:RNAP:ph -> mRNA_HslVU | Mass Action | K | true |
| mRNA_HslVU -> null | Mass Action | K | false |
| mRNA_HslVU -> HslVU | Mass Action | K | true |
| HslVU -> null | Mass Action | K | false |
| S32:RNAP:ph -> mRNA_Pro... | Mass Action | K | true |

Species Table

| Name | Initial Amount | Constant |
|---|---|---|
| DnaK | 0 | false |
| FtsH | 0 | false |
| HslVU | 0 | false |
| Pfolded | 17800 | false |
| Protease | 0 | false |
| Punfolded | 0 | false |
| Punfolded:DnaK | 0 | false |
| RNAP | 1337.6174 | false |
| mRNA_DnaK | 0 | false |
| mRNA_FtsH | 0 | false |
| mRNA_HslVU | 0 | false |
| mRNA_Protease | 0 | false |
| mRNA_s32 | 0 | false |
| null | | |

*Fig. 2B*

METHOD AND APPARATUS FOR INTEGRATED MODELING, SIMULATION AND ANALYSIS OF CHEMICAL AND BIOLOGICAL SYSTEMS HAVING A SEQUENCE OF REACTIONS, EACH SIMULATED AT A REACTION TIME DETERMINED BASED ON REACTION KINETICS

FIELD OF THE INVENTION

The present invention relates to simulation tools and, in particular, to an improved environment for modeling chemical and biochemical systems.

BACKGROUND OF THE INVENTION

The development of new drug targets by the pharmaceutical industry is time-consuming and expensive because a large number of possible targets need to be tested before the molecule or compound with the desired properties is found or formulated. Along the same argument, but not for the purpose of new drug development, are the activities or synthetic biology. Here, biological entities are designed to perform a particular function. A particular example of this case is the development of biological nanomachines that might for example be used as programmed drug delivery systems. (See J. Panyam, V. Labhasetwar, Biodegradable nanoparticles for drug and gene delivery to cells and tissue, Advanced Drug Delivery Reviews, 55 (2003) 329-347.) As in drug discovery efforts, the formulation of a compound with desired properties is difficult due to the large variety of possible targets and the even larger context or system in which they must perform their function. Currently much of the work done to investigate the properties of these compounds is done in a wet-lab requiring many tedious and error prone experiments.

Development of chemical substances and nanomachinery, in addition to being time-consuming, can generate potentially dangerous intermediate substances. For example, a molecule used as transport for a drug in a drug delivery system could by its mere presence in the organism, stimulate the overproduction of some other protein. The overexpressed protein could act as a lethal toxin for the organism. Another possible complication is that the nanomachinery itself may mutate over time and either lose its original function or worse adversely interfere with the viability of the organism.

Another problem facing the drug development activity is that, due to the cumbersome nature of experimental data collection, it is typical to limit experiments by narrowing the range of tested inputs and in general isolating the subsystem of interest. This limitation allows for the possibility that new drugs have unforeseen side-effects.

Moreover, current methods of obtaining data for biological processes are even more time-consuming than those associated with chemical processes, because the latter generally require laboratory experiments that lead to animal experiments and clinical trials. From these trials and experiments, data are obtained which, again, usually focus on a very narrow part of the biological system. Only after numerous costly trial-and-error clinical trials and constant redesigning of the clinical use of the drug to account for lessons learned from the most recent clinical trial, is a drug having adequate safety and efficacy finally realized. This process of clinical trial design and redesign, multiple clinical trials and, in some situations, multiple drug redesigns requires great expense of time and money. Even then, the effort may not produce a marketable drug. While conclusions may be drawn by assimilating experimental data and published information, it is difficult, if not impossible, to synthesize the relationships among all the available data and knowledge.

The various challenges faced by the aforementioned activities in chemical and biochemical research make it desirable to have software and methods for modeling, simulating, and analyzing biological processes in-silico rather than in-vitro or in-vivo. The goal of this approach is to provide a more comprehensive view of these biological systems prior to costly experiments and to clinical trials thereby reducing the search space for drug targets and useful nanoparticles.

The simulation of biological systems requires the use of many modes of computation such as continuous time, discrete step, hybrid, particle level among others. The need for these arises from the various simplifying assumptions made in order to make the problem tractable using today's computer technology and resources. At the most basic level, the particle based approach, every molecule in a cell is accounted for individually. Given the number of molecular components in a cell this approach is prohibitively expensive unless it is used for small relatively small number of molecules in the overall system. Approximations can be made which result in a significant reduction in the computational cost. One class of simplifications groups like-molecules and treat the entire group as one variable. This approach allows the development of probabilistic methods and well as differential ones, which are much less expensive in terms of computational cost. In effect, there is a continuum of methods varying from high fidelity, compute intensive to approximate and less expensive methods. Hybrid solvers are those that mix one or more of these methods to optimize the use of computational resources while achieving a high level of fidelity.

One such method which accounts for the random nature of molecular interactions is called a stochastic simulator; it may be used to simulate the time varying behavior of a collection of chemically interacting molecules in a chemical or biological system. In this case, the simulator maintains a list of reactions in the chemical or biological system that "could" happen and moves the state of the system forward through time in a two-step process. First, the simulator determines which reaction in the list of reactions will be the next to occur, and the time at which that reaction will occur. Second, the simulator simulates the reaction, adjusting the quantities of each type of molecule as specified by the stoichiometry of the reaction. This process is repeated iteratively as the system is marched forward in time. (See D. Gillespie, J. Phys. Chemistry, 81, 25 (1977).)

The process of deciding which reaction will occur next is more expensive both computationally and in terms of storage than the process of simulating the reaction to update the system state. In addition, current stochastic simulators are limited to modeling systems having mass-action kinetics, in which the reaction rate for each reaction is proportional to the product of the reactant quantities. Thus, determination of a reaction time for reactions having reaction kinetics (dynamics) that are not mass-action may be difficult and inaccurate.

SUMMARY OF THE INVENTION

The present invention provides a modeling and simulation environment for modeling and stochastically simulating a biological or chemical system having reactions with kinetics that are not limited to the law of mass-action. The modeling and simulation environment enables a user to create a model of a system, for example by creating a description of the system involved, and generate predictions regarding the behavior of the system using mathematics. The user can specify the chemical reactions for a system, and, for each chemical reaction, specify a probability distribution used to determine the time at which the reaction occurs. Alternatively, the probability distribution may be automatically calculated or derived from experimental data.

According to a first aspect of the invention, a method of simulating a system that comprises a plurality of chemical reactions is provided. The method comprises the steps of determining a reaction time for a first chemical reaction, which can be non-mass action, using a first probability distribution associated with the first chemical reaction and determining a reaction time for a second chemical reaction using a second probability distribution associated with the second chemical reaction. A computer-readable optical medium containing instructions for executing the steps is also provided.

The first probability distribution may be different from the second probability distribution. The first and/or second probability distribution may depend on reaction kinetics for the associated chemical reaction. The reaction kinetics generally depend on environmental conditions or variables, such as temperature, pH, pressure and other conditions.

The probability distributions may be defined by a user, automatically calculated based on kinetics of the first chemical reaction, and/or derived through data collected from at least one experiment.

The reaction time for a selected chemical reaction may be formulated by returning a random variable from the associated probability distribution.

Each probability distribution may be stored in a selected reaction object containing a definition of the associated chemical reaction.

According to another aspect of the invention, a method of simulating a system that comprises a plurality of chemical reactions is provided, which comprises the steps of determining a suitable probability distribution for a first chemical reaction in the biological system and associating the probability distribution with the first chemical reaction in a modeling environment. A computer-readable optical medium containing instructions for executing the steps is also provided.

The step of associating the probability distribution with the first chemical reaction may comprise entering the probability distribution in a reaction object for the first chemical reaction. The reaction object may then be saved in memory of the modeling environment. The simulation engine may make a call to the reaction object during simulation of the system to determine the reaction time for the first chemical reaction.

The step of associating the probability distribution with the first chemical reaction may comprise entering the probability distribution in a field of a graphical user interface associated with the first chemical reaction.

The step of determining a suitable probability distribution may comprise the steps of specifying an arbitrary distribution for the first chemical reaction, simulating the first chemical reaction at a first reaction time determined by the arbitrary distribution, and modifying the probability distribution based on said step of simulating.

According to still another aspect, a system for improved modeling and simulation of a system that comprises a plurality of chemical reactions is provided. The system comprises a modeling component comprising a graphical user interface for accepting user commands and input to construct a model of the biological system, the graphical user interface including a field for allowing a user to specify a probability distribution for at least one chemical reaction in the biological system. The system also includes a simulation engine accepting as input said constructed model of the biological system and generating as output the dynamic behavior of the biological system. The simulation engine calculates a reaction time for a chemical reaction based on a probability distribution defined by the user.

BRIEF DESCRIPTION OF THE FIGURES

The invention is pointed out with particularity in the appended claims. The advantages of the invention described above, and further advantages of the invention, may be better understood by reference to the following description taken in conjunction with the accompanying drawings, in which:

FIGS. 2A, 2B and 2C are screenshots depicting embodiments of a tabular modeling environment useful in connection with the present invention;

DETAILED DESCRIPTION OF THE INVENTION

Figure 1:
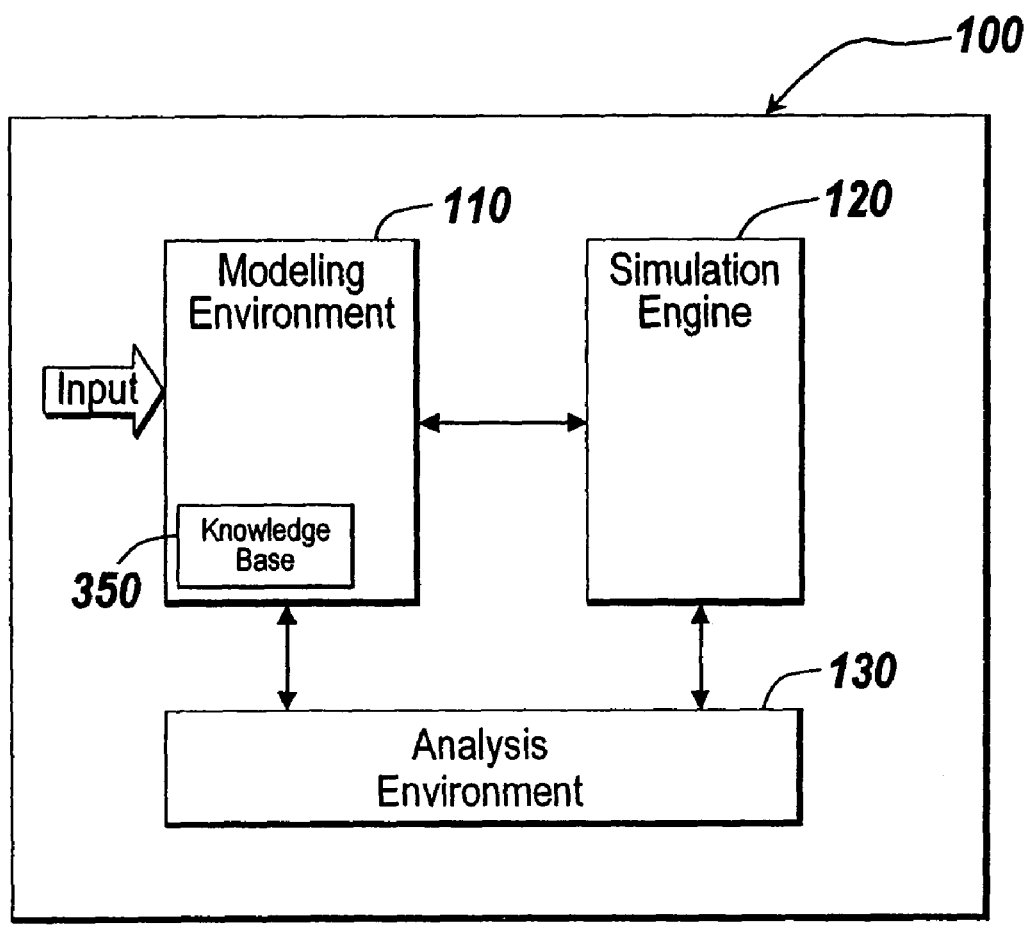
FIG. 1 is a block diagram of one embodiment of an integrated modeling, simulation and analysis environment.

The present invention enables a stochastic simulator to model systems with reactions whose kinetics are not limited to mass-action. The present invention will be described below relative to an illustrative embodiment. Those skilled in the art will appreciate that the present invention may be implemented in a number of different applications and embodiments and is not specifically limited in its application to the particular embodiments depicted herein.

In an embodiment of the invention, a system for modeling, simulating and analyzing chemical and biochemical reactions includes a modeling environment for constructing a model of a chemical or biochemical system that includes a number of chemical reactions. The system also includes a simulation engine accepting as input said constructed model of the chemical or biochemical system and generating as output the dynamical behavior of the system as modeled. An analysis environment may communicate with the simulation engine and displays this result.

An algorithm called a stochastic simulator in a simulation engine may be used to simulate the time varying behavior of a collection of chemically interacting molecules. The stochastic simulator maintains a list of reactions for a particular system and computes a reaction time for executing each reaction based on a probability distribution that may be defined for each reaction. For example, the probability distribution may depend up on the kinetics of the particular reaction or another suitable parameter. The stochastic simulator sorts the list of reactions based on the calculated putative reaction time for each reaction and executes the next reaction in the list (i.e., the reaction having the earliest reaction time). The simulator advances the simulation time to the reaction time of the executing reaction and updates parameters, such as the amount of products in the system, that change as a result of that reaction executing. Because the execution of one reaction can change the factors that influence the reaction time of other reactions, the simulator then recalculates and resorts the reaction time for reactions that change due to the execution of the most recently executed reaction. The simulator then executes the next reaction in the list, moving the simulation time forward to the reaction time of that reaction. This process is repeated many times as the system is simulated forward in time until a specified end time for the simulation is reached.

To determine the time at which each reaction occurs, the stochastic simulator may use a reaction-specific distribution suitable for the kinetics of the particular reaction. The kinetics may depend on environmental conditions or variables, including, but not limited to, temperature, pressure and/or pH, and combinations thereof. The reaction-specific probability distribution may be defined by a user and associated with the particular reaction. Alternatively, the reaction-specific distribution may be automatically calculated and associated with the particular reaction, or determined empirically through experimental data. The simulation engine may call the reaction-specific distribution during a simulation to calculate the reaction time for a particular reaction.

Referring now to FIG. 1, a high-level block diagram of one embodiment of an integrated system for modeling, simulating, and analyzing chemical reactions and biological systems that include biological processes 100 is shown. As shown in FIG. 1, the system 100 includes a modeling component designated as a modeling environment 110 in the exemplary depiction of FIG. 1, a simulation engine 120, and an analysis environment 130. The simulation engine 120 communicates with the modeling environment 110. The simulation engine 120 receives models of chemical reactions or biological processes generated using the modeling environment 110. The simulation engine 120 communicates refinements to models created in the modeling environment 110. The analysis environment 130 is in communication with both the modeling environment 110 and the simulation engine 120. The analysis environment 130 may be used to perform various types of analysis directly on models created in the modeling environment 110. Also, the analysis environment 130 may receive and process results from the simulation engine 120 representing the execution by the simulation engine 120 of a model produced in the modeling environment. In other words, the simulation engine 120 generates the dynamic behavior of the model and communicates at least some of this dynamic behavior to the analysis environment. The analysis environment 130 may provide refinements to a model in the modeling environment 110 and may provide parameters for use by the simulation engine 120 when executing a model. The interaction between the modeling environment 110, the simulation engine 120, and the analysis environment 130 will be discussed in more detail below.

The integrated system depicted in FIG. 1 may execute on a number of different computing platforms known in the art, such as, but not limited to, supercomputers, mainframe computers, minicomputers, clustered computing platforms, workstations, general-purpose desktop computers, laptops, and personal digital assistants.

The modeling environment 110 accepts input to create a model of the chemical or biochemical reaction to be simulated. In some embodiments, the modeling environment 110 accepts input contained in a file, such as a file in Systems Biology Markup Language (SBML). In others of these embodiments, the file may be in HyperText Markup Language (HTML) format, Extensible Markup Language (XML) format, a proprietary markup language, or a text file in which fields are delimited by tabs or commas. Alternatively, the modeling environment 110 may accept input produced by a user via either a command-line interface or a graphical user interface.

The modeling environment may include a plurality of reaction objects for defining each reaction in the chemical or biochemical system to be simulated. Each reaction object may encapsulate all of the information about a particular reaction that may be used when simulating the reaction.

Figure 2A:
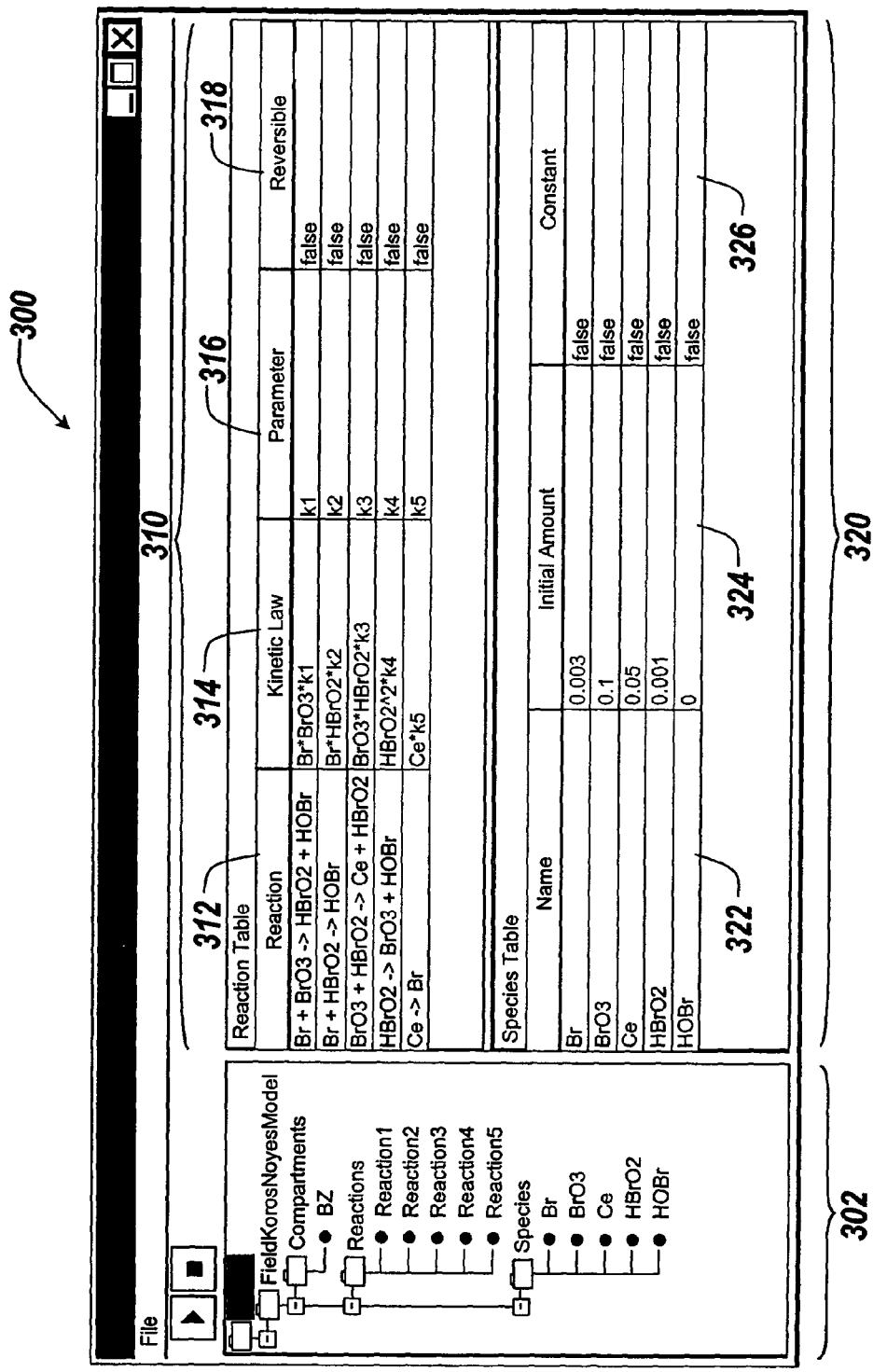

For example, a user can create a model of chemical or biochemical reactions using a graphical user interface, as shown in FIGS. 2A and 2B. FIGS. 2A and 2B depict an embodiment of a tabular graphical user interface 300 that may be used to receive input manufactured by a user for creating a model. As shown in FIGS. 2A and 2B, the user interface may include a model pane 302. In the embodiment shown in FIGS. 2A and 2B, the model pane 302 lists one or more models in a tree structure familiar to users of computers operating under control of an operating system, such as the WINDOWS operating system manufactured by Microsoft Corp. of Redmond, Wash., or another suitable operating system using graphical controls. In the particular embodiment depicted by FIG. 2A, a single model of a chemical reaction is contained in the model pane 302, indicated by the folder labeled "FieldKorosNoyesModel". That model contains three subfolders: "Compartments"; "Reactions"; and "Species". The subfolders represent pieces of the modeled reaction. Other graphical user interface schemes may be used to present this information to the user of a system 100. In some embodiments, the model pane 302 may display a number of folders representing models. User selection of a particular folder causes the system to display folder in the model pane 302 that represent pieces of the reaction, e.g., compartments, reactions, and species. In still other embodiments, each model and all components of all models may be displayed in the model pane 302 and each model may be associated with a "radio button." Selection of the radio button associates with a model causes that model and its constituents to be actively displayed. In some of these embodiments, unselected models are displayed in grey type, or may have a transparent grey overlay indicating that they are not currently the active model.

Referring back to FIG. 2A, the illustrative graphical user interface 300 also includes a reaction table 310, and a species table 320. The reaction table 310 is associated with the "Reactions" folder displayed in the model pane 302. Similarly, the species table 320 is associated with the "Species" folder displayed in the model pane 302. In some embodiments, collapsing the associated folder causes the table to not be displayed. The respective tables may be displayed in their own graphical user interface window, rather than in the same window as the graphical user interface 300, as shown in FIG. 2A.

The reaction table 310 lists each reaction present in a modeled biological process or chemical reaction. In the embodiment shown in FIG. 2A, the modeling environment 300 displays reactions present in the Field-Koros-Noyes model of the Belousov-Zhabotinsky reaction and includes four columns: a reaction column 312, a kinetic law column 314, a parameter column 316, and a reversible column 318. Each row of the reaction table 310 corresponds to a particular reaction. The number and format of columns displayed by the reaction table may be selected by the user. In other embodiments, the modeling environment 110 may select the number and format of columns to display based on the type of reaction selected by the user.

Referring back to the embodiment shown in FIG. 2A, the reaction column 312 displays a reaction represented in an abstract format, e.g., Ce→Br. In other embodiments, the reaction may be represented as a differential equation, in stochastic format, or as a hybrid of two or more of these formats. In some embodiments, the reaction table includes a column identifying modifiers of the reaction. For example, some reactions can be catalyzed by a substance. This may be represented in the tabular format as Ce–m(s)→Br, meaning that the presence of the species "s" accelerates the conversion of Ce into Br.

In the embodiment shown in FIG. 2A, the reaction table 310 also includes a kinetic law column 314 which identifies the kinetic law expression the identified reaction follows. In the embodiment shown in FIG. 2A, the kinetic law associated with the Ce→Br reaction is "Ce*k5," meaning that Ce is consumed at a rate controlled by the parameter "k5" and the amount of Ce present. In the embodiment shown in FIG. 2A, the parameters for the kinetic law expression are listed in the parameter column 316. In some embodiments, the reaction table 310 includes a column identifying the name of the kinetic law associated with a particular reaction, e.g. "mass action" or "Michaels-Menten." In other embodiments, the reaction table 310 includes a column identifying the units in which the kinetic law parameters are expressed, e.g., 1/seconds, 1/(moles*seconds), etc.

Still referring to the embodiment shown in FIG. 2A, the reaction table 310 includes a reversible column 318, which indicates whether the associated reaction is reversible. A reversible reaction is one which occurs in either direction, i.e. Ce<->Br. In some embodiments the reaction table 310 may include a column identifying dynamics of the reaction, e.g., "fast" or "slow." In some of these embodiments, the rapidity with which a reaction occurs is identified on a scale of 1 to 10. In still other embodiments, the user may be presented with a slide control that allows the rapidity of various reactions to be set relative to one another. In still further embodiments, the reaction table 310 may include a column for annotations or notes relating to the reaction.

In one embodiment, the model environment may allow for simulation of a reaction with non-mass action kinetics. As used herein, a reaction with non-mass action kinetics refers to a reaction with a reaction rate that is approximated by non-mass action kinetics. To model non-mass action reactions, a reaction distribution, known as a probability distribution, may be specified, by a user or suitable program, for each reaction listed in the table. The probability distribution is used during simulation of the modeled system to determine a reaction time for a particular reaction in the model. When simulated stochastically, a reaction will occur at a random time determined according to a probability distribution, which depends on a parameter of the reaction, such as the kinetics of the particular reaction, as well as the execution of previous reactions in the system. For example, for reactions having mass-action kinetics, in which the reaction rate is proportional to the product of the reactant quantities, the next reaction occurrence time during a simulation may be determined by drawing a random number from an exponential distribution. For reactions having kinetics that are not mass-action, another probability distribution may be appropriate. The user can specify a probability distribution that is suitable for the particular kinetics of each reaction. The reaction kinetics of a chemical reaction may depend on environmental conditions or variables, including, but not limited to, temperature, pressure and/or pH as well as combinations of these variables. A probability distribution of a later reaction in a system may also be impacted by an earlier reaction, i.e., the time of the earlier reaction as well as the execution and result of the earlier reaction.

Alternatively, the probability distribution may be automatically calculated by a program in the model environment. The probability distribution program may automatically calculate a suitable probability distribution for the selected reaction based on kinetic law. For example, the particular probability distribution may depend on the number of reactants, the number of products and the number of elementary steps in a particular reaction.

According to another example, the particular probability distribution associated with a particular reaction may be derived from experimental data. For example a program may collect data from experiments and calculate a probability distribution, which is fed back to the model environment and associated with a model of that reaction.

One skilled in the art will recognize that any suitable means for determining a suitable probability distribution for a non-mass action reaction may be used in accordance with the teachings of the invention.

Any suitable probability distribution known in the art may be used to determine when the reaction occurs. The probability distribution preferably has a curve forming an area of one under the curve, and is not negative anywhere.

Figure 2C:
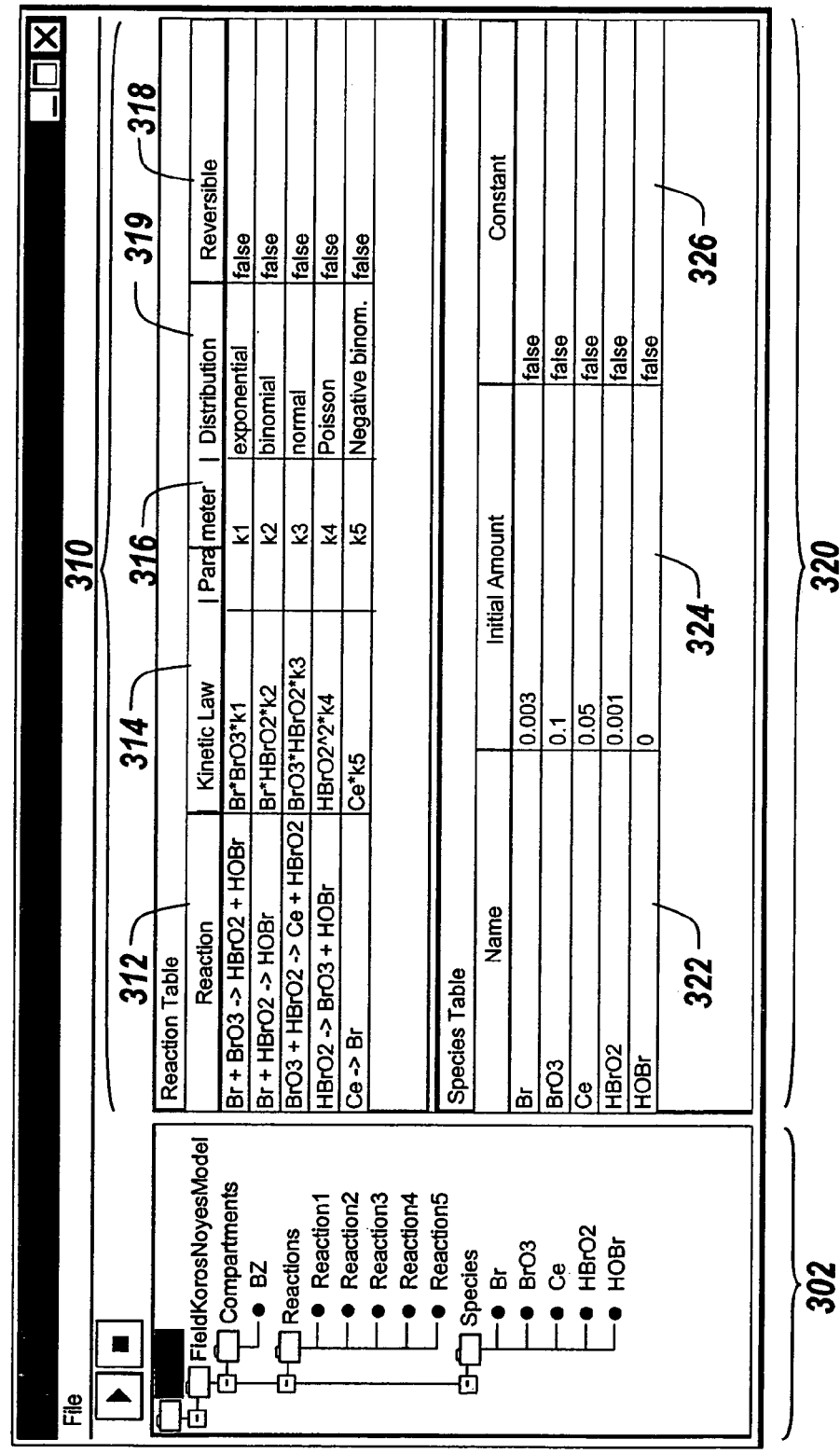

For example, as shown in FIG. 2C, the reaction table 310 may include a distribution column 319, which indicates a suitable probability distribution for the associated reaction. The probability distribution may be specified using a MATLAB vector or through another suitable format. If the user does not specify a particular probability distribution, the modeling environment may assign a default distribution, such as an exponential distribution, to each reaction. Alternatively, the simulation engine may wait to simulate the model stochastically until the modeling environment contains sufficient information to computer a reaction time. Alternatively, the user can specify a suitable distribution in a separate graphical user interface, or through other means known in the art.

If an appropriate probability distribution is not known for a particular reaction kinetics (i.e., dynamics), the user can research and experiment with different distributions. For example, the user can specify arbitrary distributions to be used, then determine which distribution is suitable for the particular reaction. In this manner, users can experiment with different distributions easily as they research the question of appropriate distribution structure for the kinetics of the particular reaction.

Alternatively, as described above, a separate program may automatically calculate a suitable probability distribution, or derive a probability distribution based on experimental data. The model environment may automatically populate the field associated with the particular reaction in the distribution column 319 with the calculated probability distribution.

The modeling environment 300 shown in FIG. 2A also displays a species table 320. In the embodiment shown in FIG. 2A, the species table 320 includes a name column 322, an initial amount column 324, and a constant column 326. The species table depicts the initial conditions and amounts of material used in the modeled biological process or chemical reaction. Thus, in the embodiment shown in FIG. 2A, the modeled biological process begins with 0.003 molar units of bromine, i.e., 0.003 multiplied by Avrogado's number. The constant column 326 is set to "true" if the model should assume that there is an infinite supply of a particular species. In other embodiments the species table 320 includes other columns such as a column identifying units (e.g., moles, molecules, liters, etc.), whether a particular species is an independent variable in the model (i.e., whether the species is an input to the system), a column for annotations, or a column for notes.

In some embodiments, the modeling environment 300 accepts as input a file in a markup language and converts that file into a graphical display of the sort depicted in FIG. 2A. For example, one representation of the Field-Koros-Noyes model of the Belousov-Zhabotinsky reaction in markup language that corresponds to the particular embodiment shown in FIG. 2A is shown in Appendix A to this document.

For example, a process may be provided that uses the information embedded in the tags of the markup language file, e.g., <reaction name="Reaction5" reversible="false">, to generate the tabular form of the model shown in FIGS. 2A, 2B and 2C. In some of these embodiments, a web browser may be modified to parse files containing models written in markup language in order to create the tabular form of the model shown in FIGS. 2A, 2B and 2C. In other embodiments, a process may accept the model as input and generate as output code that is directly executable on a processor, such a code written in the C programming language.

The model of a chemical or biochemical reaction created in the modeling environment may be converted into executable code. Conversion of a model into executable code allows the executable code to be transmitted to multiple computers via a network for execution on those computers. In these embodiments computers may be connected via a number of network topologies including bus, star, or ring topologies. The network can be a local area network (LAN), a metropolitan area network (MAN), or a wide area network (WAN) such as the Internet.

In these embodiments, a master server parses a model written in markup language. The model may be retrieved from a hard disk or from another computer accessed via a network connection. In other embodiments, the model is input by a user using a tabular user input such as the one shown in FIGS. 2A, 2B and 2C or a graphical user interface such as the one shown in FIG. 3. The master server parses the model to produce executable code. The executable code produced by the master server may be compiled code, such as code written in C, C+, C++, or C# and compiled to run on a target platform or the executable code produced by the master server may be a in a bytecode language such as JAVA. In some embodiments, the executable code is transmitted to one or more computers via a network connection. The one or more computers execute the code representing the model and return the generated result to the master server. The master server may store the retrieved results for later analysis. In some embodiments, the master server displays a graphical representation of each of the received results. In one embodiment, this technique is used to conduct Monte Carlo type analysis. In certain of these embodiments, the master server may collect and display each data point received and display each data point graphically in real-time.

FIG. 2B depicts in tabular form reactions for simulating the *E. Coli* heat shock response model according to an illustrative embodiment of the invention. As described above in connection with FIG. 2A, the upper table displays the various reactions involved in transcription and translation of the heat shock proteins as well as the interactions of heat shock proteins with unfolded (or denatured) proteins. As depicted in FIG. 2B, all reactions in the *E. Coli* heat shock response model have mass action kinetics and some are reversible, while some are not. Another method of representing chemical or biochemical reactions is by way of a block diagram.

Figure 3:
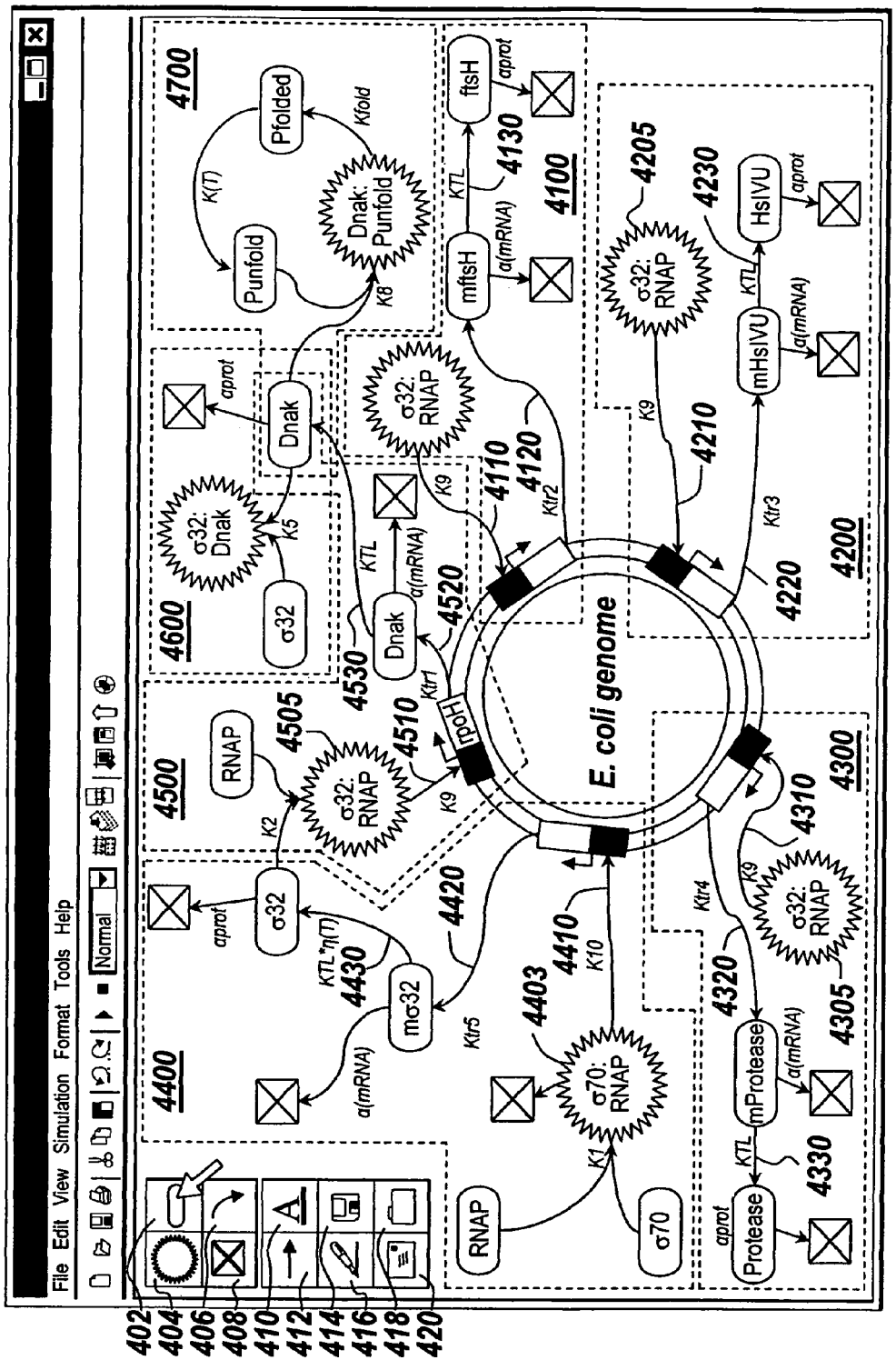
FIG. 3 is a screenshot of one embodiment of a graphical user interface that facilitates construction of block diagram representations of chemical reactions or biological processes.

In still other embodiments, the modeling environment 300 allows a user to represent a biological process or chemical reaction as a block diagram. FIG. 3 depicts an embodiment of a block diagram modeling environment. In the embodiment depicted in FIG. 3, a block diagram showing heat shock reaction in *E. Coli* bacteria is under construction. As is well known, heat shock response in *E. coli* is a protective cellular response to heat-induced stress. Elevated temperatures result in decreased *E. coli* growth, in large part, from protein unfolding or misfolding. The heat shock response, via heat shock proteins, responds to heat induced stress by refolding proteins via chaperones or by degrading nonfunctional proteins via proteases.

The block diagram shown in FIG. 3 depicts the expression of five particular gene sequences involved in the heat shock response. In part, FIG. 3 depicts pathways 4100, 4200, 4300 for the expression of proteases involved in heat shock response. Pathways 4100, 4200, 4300 represent the expression of heat shock proteins ftsH, Hs1VU and other proteases, respectively. The pathways 4100, 4200, 4300 are activated by the interaction 4105, 4205, 4305 of $\sigma^{32}$ with RNA polymerase at the promoter of the respective sequence. Each pathway 4100, 4200, 4300 depicts the transcription 4120, 4220, 4320 of the mRNA mediated 4110, 4210, 4310 by the $\sigma^{32}$ and RNA polymerase interaction 4105, 4205, 4305 at the promoter and the subsequent translation 4130, 4230, 4330 of the protease. The heat shock proteases, including ftsH and Hs1VU, serve to degrade proteins rendered nonfunctional by heat stress. Similarly, the diagram depicts the pathways 4400, 4500 involved in the expression of the heat shock proteins $\sigma^{70}$ and DnaK, respectively. The expression of the $\sigma^{32}$ protein is activated 4410 by the interaction 4403 of $\sigma^{70}$ and RNA polymerase at the promoter. The $\sigma^{32}$ mRNA is transcribed 4420 and, subsequently, $\sigma^{32}$ is translated 4430. In a closely related pathway 4500, the heat shock protein DnaK is translated. The interaction 4505 of $\sigma^{32}$ and RNA polymerase at the promoter activate 4510 the transcription 4520 of DnaK mRNA and, subsequently, the translation 4530 of DnaK. DnaK, in turn, may either interact 4600 with $\sigma^{32}$ so as to stabilize $\sigma^{32}$ or, alternatively, may refold 4700 the proteins unfolded by heat stress.

A block diagram editor, which is a component of the modeling environment, allows users to perform such actions as draw, edit, annotate, save, and print out block diagram representations of dynamic systems. Blocks are the fundamental mathematical elements of a classic block diagram model. In some of these embodiments, the modeling environment includes two classes of blocks, non-virtual blocks and virtual blocks. Non-virtual blocks are elementary dynamic systems, such as the $\sigma^{32}$ and RNA polymerase interaction 4105, 4205, 4305. A virtual block may be provided for graphical organizational convenience and plays no role in the definition of the system of equations described by the block diagram model. For example, in the block diagram of the heat shock mechanism in *E. Coli* bacteria depicted in FIG. 3, gene transcription mediated by σ32 to produce proteins, represented by 4100, 4200, and 4300, may be represented as a single, virtual block. In this case, the virtual block adds hierarchy to a model for the purpose of improving the readability of models.

The block diagram editor is generally a graphical user interface (GUI) component that allows drafting of block diagram models representing a chemical or biochemical reaction by a user. FIG. 3 depicts an embodiment of a GUI for a block diagram editor that features a floating element palette. In the embodiment shown in FIG. 3, the GUI tools include various block tools 402, 404, 408, various wiring line connection tools 406, 412, an annotation tool 416, formatting tool 410, a save/load tool 414, a notification tool 420 and a publishing tool 418. The block tools 402, 404, 408 represent a library of all the pre-defined blocks available to the user when building the block diagram. Individual users may be able to customize this palette to: (a) reorganize blocks in some custom format, (b) delete blocks they do not use, and (c) add custom blocks they have designed. The blocks may be dragged through some human-machine interface (such as a mouse or keyboard) on to the window (i.e., model canvas). The graphical version of the block that is rendered on the canvas is called the icon for the block. There may be different embodiments for the block palette including a tree-based browser view of all of the blocks. In these embodiments, the floating element palette allows a user to drag block diagram elements from a palette and drop it in place on the screen. In some of these embodiments, there may also be a textual interface with a set of commands that allow interaction with the graphical editor. For example, dragging a polymerase block to the model may cause the system to prompt the user for the protein to be used in the polymerase reaction.

Using this textual interface, users may write special scripts that perform automatic editing operations on the block diagram. A user generally interacts with a set of windows that act as canvases for the model. There can be more than one window for a model because models may be partitioned into multiple hierarchical levels through the use of subsystems. In still other embodiments, only a textual interface may be provided for facilitating the user's construction of the block diagram.

The modeling environment 300 may also offer a variety of other GUI tools that improve the ability of users to build and manage large block diagrams. For example, wiring line connection tools 406, 412 allow users to draw directed lines that connect the blocks in the model's window. Connections may be added through various other mechanisms involving human-machine interfaces, such as the keyboard. The annotation tool 416 allows users to add notes and annotations to various parts of the block diagram. The formatting tool 410 enables users to perform various formatting operations that are generally available on any document editing tool. The save/load tool 414 allows a created block diagram model to be saved in a library or other suitable location for future use. A publishing tool 418 may be provided to enable the viewing of the block diagram as a document that can be published in any standard document formats (examples: PostScript, PDF, HTML, SBML, XML, SGML, SBML etc.). A notification tool 420 allows a user working on a block diagram to send a message to another user. In some embodiments, the notification tool 420 causes the current version of the block diagram, to be mailed to the specified user.

Those skilled in the art will also recognize that block-diagram packages offer scripting languages for writing out programs that automatically carry out a series of operations that would normally require interaction with the GUI, such as block addition, block deletion, starting and terminating execution, or modifying block attributes, etc.

The modeling environment 300 may also offer a variety of other GUI tools that improve the ability of users to build and manage large block diagrams. Examples of such GUIs include: (a) a Finder that helps find various objects such as blocks and lines within a block-diagram, (b) a Debugger that helps debug the execution of block-diagrams, (c) a Revision Control UI for managing multiple revisions of the block-diagram, and (d) a Profiler for viewing timing results while executing a block-diagram.

In some embodiments, the modeling environment 110 includes a knowledge base 350 that aids in construction of a model. In some of these embodiments, the knowledge base 350 contains models for various reactions, e.g. glycolysis. In these embodiments, when a user begins to input reactions consistent with a model for glycolysis, the knowledge base 350 may enter the remaining reactions for the user. Alternatively, the knowledge base 350 may offer different models of the reaction to the user. In some of these embodiments, the offered models represent the target reaction with varying levels of detail. In other embodiments, the knowledge base 350 may insert parameters or indications of reversibility for entered reactions. For example, the knowledge base 350 may specify a probability distribution that is suitable for the particular kinetics/dynamics of one or more entered reactions. The knowledge base 350 may also provide assistance to a user inputting a block diagram representation of a chemical or biochemical reaction. For example, the knowledge base 350 may prevent a user manufactured by connecting blocks inconsistent with the modeled reaction. Examples of publicly-available databases that may be used to facilitate generation of models include the Swissprot database, the National Center for Biotechnology Information (NCBI), the Research Collaboratory for Structural Bioinformatics Protein Data Bank (RCSB PDB), and the Kyoto Encyclopedia of Genes and Genomes (KEGG). Alternatively, the user may provide private databases to act as a knowledge base 350 for facilitating creation of models.

In other embodiments the knowledge base 350 may be used to facilitate further or broader understanding of the modeled reaction. For example, referring to the block diagram representation of the heat shock reaction in *E. Coli* bacteria, the knowledge base 350 can be used to identify other reactions in the heat shock reaction that use, or are impacted by, σ70. Alternatively, the knowledge base 350 may identify other reactions for *E. Coli* in which σ70 plays a part, e.g., chemotaxis. In this way, a broader understanding of the functioning of *E. Coli* in various environments can be achieved.

In still other embodiments, the modeling environment 110 provides libraries from which blocks may be selected and included in a model. Models referenced by virtual or non-virtual blocks in a model, whether or not part of a library, are included in the model for execution. For embodiments in which executable code is generated, code representing the referenced models is also generated.

Once a block diagram model has been constructed within a modeling environment 110 using the tools described above, the chemical or biological reaction may be simulated by executing the model. An execution engine carries out the task of compiling and linking the block diagram to produce an "in-memory executable" version of the model that is used for generating code and/or simulating or linearizing a block diagram model. Execution of the block-diagram is also referred to as simulation. Model execution is carried out over a user-specified time span for a set of user-specified inputs. The execution begins when the block diagram is compiled. The compile stage marks the start of model execution and involves preparing data structures and evaluating parameters, configuring and propagating block characteristics, determining block connectivity, and performing block reduction and block insertion. The preparation of data structures and the evaluation of parameters create and initialize basic data-structures needed in the compile stage. For each of the blocks, a method forces the block to evaluate all of its parameters. This method is called for all blocks in the block diagram. If there are any unresolved parameters, execution errors are thrown at this point. During the configuration and propagation of block and port/signal characteristics, the compiled attributes (such as dimensions, data types, complexity, or sample time) of each block (and/or ports) are setup on the basis of the corresponding functional attributes and the attributes of blocks (and/or ports) that are connected to the given block through lines. The attribute setup is performed through a process during which block functional attributes "ripple through" the block diagram from one block to the next following signal connectivity. This process (referred to herein as "propagation"), serves two purposes. In the case of a block that has explicitly specified its block (or its ports') functional attributes, propagation helps ensure that the attributes of this block are compatible with the attributes of the blocks connected to it. If not, an error is issued. Secondly, in many cases blocks are implemented to be compatible with a wide range of attributes. Such blocks adapt their behavior in accordance with the attributes of the blocks connected to them. This is akin to the concept of polymorphism in object-oriented programming languages. The exact implementation of the block is chosen on the basis of the specific block diagram in which this block finds itself. Included within this step are other aspects such as validating that all rate-transitions within the model yield deterministic results and that the appropriate rate transition blocks are being used.

The compilation step also determines actual block connectivity. In this step, the virtual blocks in the block diagram, which play no semantic role in the execution of a block diagram, are optimized away (removed) and the remaining non-virtual blocks are reconnected to each other appropriately. This compiled version of the block diagram with actual block connections is used from this point forward in the execution process. The way in which blocks are interconnected in the block diagram does not necessarily define the order in which the equations (methods) corresponding to the individual blocks will be solved (executed). The actual order is partially determined during the sorting step in compilation. Once the compilation step has completed, the sorted order cannot be changed for the entire duration of the block diagram's execution.

Following the compilation stage is the model link stage. After linking has been performed, code may or may not be generated. If code is generated, the model is simulated/executed through accelerated simulation mode in which the block diagram model (or portions of it) is translated into either software modules or hardware descriptions (broadly termed code). If this stage is performed, then the stages that follow use the generated code during the execution of the block diagram. If code is not generated, the block diagram may execute in interpretive mode in which the compiled and linked version of the block diagram may be directly utilized to execute the model over the desired time-span. This interpretive mode of execution is suitable for getting fine-grained signal traceability. There are several different advantages to execution through code generation. Execution of generated code can be more efficient than interpretive execution because of fewer data-structures and lesser internal messaging in the engine, although the increased efficiency generally comes at the cost of decreased execution traceability. Simulation of hardware descriptions during execution can help identify and resolve bugs in the software stage of a design project. Such bugs prove much more expensive to track and fix once the system has been implemented in hardware. Additionally, block diagram modeling software can be integrated with other software environments that are suitable for modeling and simulating special classes of systems. Models can be tested directly in hardware thereby making prototyping of new systems fast and cost-effective. Those skilled in the art will recognize that when users generate code, they may choose to not proceed further with the block diagram's execution. They may choose to take the code and deploy it outside of the confines of the modeling software environment. This is normally the last step in the design of dynamic systems in a block diagram software package.

In one particular embodiment the modeling environment 110 provides a tool allowing a user to select the complexity with which a model executes. Referring back to FIG. 3 as an example, a user can be provided with a choice of executing pathway 4100 as a simple input-output block or executing pathway 4100 in the more detailed form shown in FIG. 3.

Referring back to FIG. 1, the model created in the modeling environment 110 can be used by the simulation engine 120. Dynamic systems, such as biological processes and chemical reactions, are typically modeled as sets of differential, difference, algebraic, and/or recursive equations. At any given instant of time, these equations may be viewed as relationships between the system's output response ("outputs"), the system's input stimuli ("inputs") at that time, the current state of the system, the system parameters, and time. The state of the system may be thought of as a numerical representation of the dynamically changing configuration of the system. For instance, in a physical system modeling a simple pendulum, the state may be viewed as the current position and velocity of the pendulum. Similarly, a signal-processing system that filters a signal would maintain a set of previous inputs as the state. The system parameters are the numerical representation of the static (unchanging) configuration of the system and may be viewed as constant coefficients in the system's equations. For the pendulum example, a parameter is the length of pendulum and for the filter example; a parameter is the values of the filter taps. A simulation engine useful in connection with the present invention is Simulink, available from The MathWorks, Inc. of Natick, Mass.

Types of mathematical models used in the study of dynamic systems include differential equations, difference equations, algebraic equations, and hybrid models. For modeling biological processes and chemical reactions, a stochastic model may be useful. This model describes systems using stochastic techniques, such as Gillespie, Gibson/Bruck, and τ-leaping.

For example, the Gillespie stochastic technique uses an algorithm to numerically simulate the time evolution of a given chemical system. In the Gillespie technique, reaction events given selected probabilities of occurring, and the events which occur change the probabilities of subsequent events. The algorithm determines, for a system in a given state, the next reaction to occur and the time that the next reaction occurs using probability. The algorithm is based on a quantity P(t,u), which is the probability that a reaction u will occur at the time interval t. The probabilities are based on the classical rate coefficients (k), the volume of the container, which can be a cell, a partition of a cell, a compartment of the cell, such as the nucleus or other organelles, or other container, and the concentration of reactants in a given reaction. Once a time and reaction have been computed, the method carries out the reaction, i.e., it updates the state of the system to reflect the transformation of reactants into products, then increments the time by t and determines another reaction to occur and when the reaction will occur. The Gillespie technique is described in detail in the article: Gillespie, D. T. 1977, *Exact Stochastic Simulation of Coupled Chemical Reactions*, Journal of Physical Chemistry, vol. 81, pp. 2340-2361.

The Gibson/Bruck stochastic technique is a variation of the Gillespie algorithm and described in the journal article Gibson, M. A., and J. Bruck, *Efficient Exact Stochastic Simulation of Chemical Systems with Many Species and Many Channels,* 2000 Journal of Physical Chemistry A, vol. 104, pp. 1876-1889.

One skilled in the art will recognize that any suitable stochastic technique for simulating the time evolution of a given chemical system may be utilized in the present invention. These techniques are useful when the continuous approximation implied by ODE/DAE systems is not applicable. This may be the case when dealing with small molecule counts, such as RNA polymerase binding to DNA to transcribe a particular gene. An example of a chemical equation that could be treated stochastically is shown in the reactions table of FIG. 2B, e.g., s32+Dnak→s32:Dnak. This equation indicates that one molecule of s32 bonds with one molecule of Dnak. When simulated stochastically, this reaction occurs at a random time determined according to the probability distribution associated with that reaction, as described above.

Inherent in four of the classes of systems (ODE, difference equations, algebraic equations and composite) is the notion of system sample time. The sample-time is the time interval at which the inputs, state, or outputs (collectively referred to as the results) of the system are traced as time progresses. Based on sample times, a system can be described as a discrete-time system, continuous-time system and hybrid system. As noted above, stochastic systems occur at a random time determined by a reaction-specific operative probability distribution.

A discrete-time system is a system in which the evolution of the system results is tracked at finite intervals of time. In the limit as the interval approaches zero, the discrete-time system becomes a continuous-time system. The intervals of time may be periodic or non-periodic. Sometimes, non-periodic rate systems, such as stochastic systems, are referred to as non-uniform rate systems meaning that there is no periodic rate at which the response can be tracked. A continuous-time system is a system in which the evolutions of the system results are continuously changing. Continuous-time signals change during numerical integration. An example of a continuous-time system is one described by an ODE. There can also be algebraic or composite continuous-time systems. A hybrid system is a system with both discrete-time and continuous-time elements.

If a system has only one sample time, it is said to be single-rate. If a system has multiple sample times, it is said to be multi-rate. Multi-rate systems can be evaluated (executed) using either a single-tasking form of execution or a multi-tasking form of execution. When multi-tasking execution is used, it conforms to rate monotonic scheduling principals as defined by Liu, C. L., and LAYLAND, J. W. *Scheduling Algorithms for Multiprogramming in a Hard-Real-Time Environment*. ACM 20, 1 (January 1973), 46-61. Systems may also be categorized by the type of numerical integration solver being used. A fixed-step system is one that uses a fixed-step solver. Fixed-step solvers typically use explicit methods to compute the next continuous state at fixed periodic intervals of time. A variable-step system is one that is using a variable-step solver. A variable-step solver can use either implicit or explicit methods to compute the next continuous state at non-periodic intervals of time. Generally, variable-step solvers use a form of error control to adjust the interval size such that the desired error tolerances are achieved.

As noted previously, stochastic reactions occur at a random time based on a reaction-specific probability distribution, which do not neatly fit either a fixed-step type of solver or a continuous-time solver. In order to adequately model systems including stochastic reactions, either alone or as part of a hybrid system including both stochastic and either fixed-solver elements or variable-solver elements, the following steps may be taken.

Figure 4:
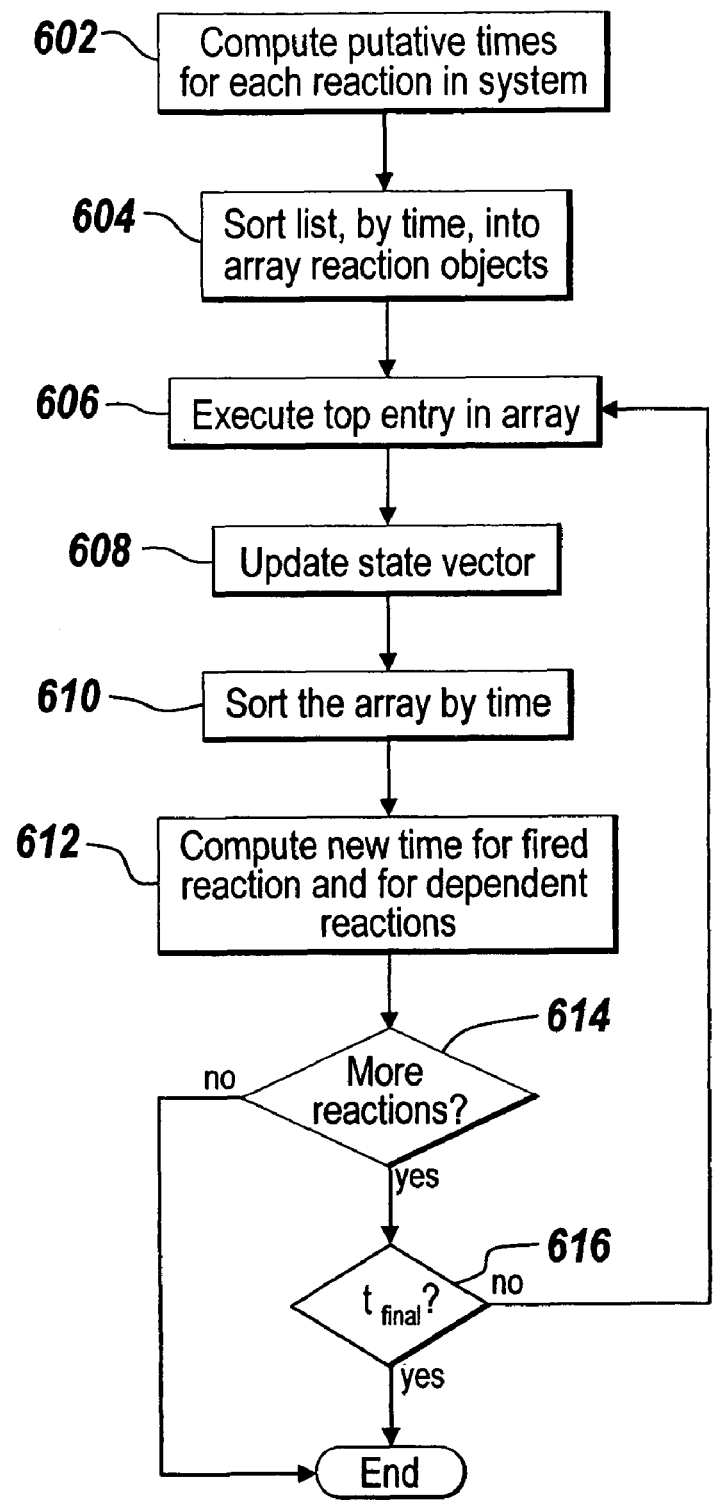
FIG. 4 is a flowchart depicting one embodiment of the steps taken to simulate a modeled biological process or chemical reaction using the stochastic solver method.

FIG. 4 illustrates the steps involved in simulating a biological or chemical system modeled using the modeling environment 100. In a first step, the simulation determines putative times for each reaction in the model (step 602) using the probability distribution associated with each reaction. During simulation, the simulation engine 120 retrieves the information for a particular reaction from a reaction object that includes information defining that reaction. In particular, the simulation engine 120 makes a call to a reaction object to retrieve the probability distribution associated with that particular reaction, which may be defined by the user, determined automatically or derived from experiments, as described above. The call to the reaction object returns a random variable drawn from the probability distribution associated with the particular reaction, so that each reaction uses a distribution appropriate for the kinetics of that reaction. In this manner, the simulation engine can accurately simulate systems with arbitrary reaction kinetics, as long as an appropriate distribution can be created for each reaction.

Once putative reactions times are computed for each reaction in the system using a probability distribution particular to each reaction, the times are sorted, by putative occurrence time, into a state array (step 604). In one embodiment, the state array is an array of pointers sorted by occurrence time, each of the pointers pointing to the object to be executed at that point in model simulation. Once sorted, the object identified by the first entry in the array is executed (step 606).

Because execution of the top object may affect the amount of species present in the modeled system or the putative reaction times for specific reactions in the table, the putative time for each of the entries in the state array is recalculated (step 608) and the state array is resorted (step 610).

The simulation engine 120 checks for additional reactions to execute (step 614). If additional reactions exist, the simulation engine 120 checks to determine in the final simulation time has been reached (step 616). If not, the simulation engine 120 executes the next entry in the state array (step 606). Otherwise, the simulation terminates. One skilled the art would recognize that other scheduling methodologies may be used.

Referring again to FIG. 1, the results generated by the simulation engine 120 may be used by an analysis environment 130. In other embodiments, the analysis environment 130 operates directly on a model, for example, to generate a steady-state value for a modeled system instead of simulating the system. In some of these embodiments, the analysis tool 120 does this by setting the derivative of all differential equations to 0 and solving the system algebraically. In others of these embodiments, the analysis engine performs a flux-balance analysis, as is known in the art, to determine the steady-state value of a system. Other well-known forms of analysis that may be employed by the analysis environment 120 include using non-linear solvers, sensitivity analysis, bifurcation analysis, parameter scans, parameter estimation and network inference analysis. The result of these analyses may be provided to the simulation engine 120 as input for its calculations.

The analysis environment 130 may further process the results generated by the simulation engine 120 or it may display the results visually or auditorially. For example, the analysis environment 120 may use graph visualization techniques to identify to a user similar pathways. In some embodiments the analysis environment 130 interfaces with data acquisition hardware (not shown in FIG. 1) which allows the analysis environment 130 to compare the generated results with experimental data. In these embodiments, data gathered from an ongoing experiment is used to correct or generate a model of the reaction that is occurring in situ. In some embodiments the experiment is conducted on a microarray or a gene chip. For example, if the existence of a given protein is predicted by a model but data acquired from the experiment indicates that the protein does not exist, the analysis tool 130 may signal a user, either auditorially or visually, that the in situ experiment and the predicted response differ. For embodiments in which the experiment is conducted on a microarray, the gathered data may differ between microwells. In these embodiments, the analysis tool may average the value of the gathered data. In others of these embodiments, the analysis environment 130 may signal a difference if the data from a single microwell differs from the model's predicted response. In some embodiments, the amount of tolerable difference between the in situ experiment and the predicted result is user-configurable. In other embodiments, the analysis tool transmits the gathered data to the modeling environment 110 so that the model may be modified to account for the difference. In still other embodiments, the analysis environment 130 graphically displays the expected result of the experiment and data gathered from the experiment.

In other embodiments, the data acquisition hardware allows the analysis tool to control an experiment that is in progress based on the results generated by the simulation engine 120. These embodiments may be useful in construction of nanomachinery. In these embodiments, a model may call for in situ temperature to be at 102 degrees Fahrenheit. If a thermocouple measuring temperature of the in situ environment indicates that the temperature has fallen below 102 degrees Fahrenheit, more heat may be applied to the experiment.

Data acquisition hardware may include any of a number of hardware devices compatible with the computing platform executing the integrated modeling, simulation, and analysis environment 100. For example, in embodiments in which the environment 100 executes on a personal computer, the data acquisition hardware interfaces with the local system bus 220. In embodiments such as those shown in FIG. 2B, the data acquisition hardware interfaces with the HyperTransport bus, Rapid I/O bus, or Infiniband. The data acquisition hardware can communicate with instruments and experiments that use GPIB (IEEE-488, HPIB), VISA, TCP/IP, and UDP standards.

Although the systems and methods of the present invention have been described above as executing on a single machine, they may also be used in a client-server environment such as X-Windows or Microsoft Terminal Services. The modeling environment 110, simulation engine 120, and analysis environment 130 may each execute on separate machines, or they may be aggregated in any combination between machines. For example, in one particular embodiment, the modeling environment 110 and the analysis environment 0 130 execute on a "client" machine while the simulation engine executes on a "server" machine. In these embodiments, the computers may be connected via a number of network topologies including bus, star, or ring topologies. The network can be a local area network (LAN), a metropolitan area network (MAN), or a wide area network (WAN) such as the Internet. The respective computers may connect to the network 180 through a variety of connections including standard telephone lines, LAN or WAN links (e.g., T1, T3, 56 kb, X.25), broadband connections (ISDN, Frame Relay, ATM), and wireless connections. Connections can be established using a variety of communication protocols (e.g., TCP/IP, IPX, SPX, NetBIOS, NetBEUI, SMB, Ethernet, ARCNET, Fiber Distributed Data Interface (FDDI), RS232, IEEE 802.11, IEEE 802.11a, IEE 802.11b, IEEE 802.11g and direct asynchronous connections).

An embodiment of the present invention relates to a computer storage product including a computer-readable medium having computer code thereon for performing various computer-implemented operations. The media and computer code may be those specially designed and constructed for the purposes of the present invention, or they maybe of the kind well known and available to those having skill in the computer software arts. Examples of computer-readable media include, but are not limited to: magnetic media such as hard disks, floppy disks, and magnetic tape; optical media such as CD-ROMs, CD-R/RW discs, DVD-ROMs, DVD-RAMs, and holographic devices; magneto-optical media such as floptical disks; solid-state memories such as flash drives, memory sticks, xD cards, MultiMedia cards, and Smart Media cards; and hardware devices that are specially configured to store and execute program code, such as application-specific integrated circuits ("ASICs"), field-programmable gate arrays (FPGAs), programmable logic devices ("PLDs"), read only memories ("ROMs"), random access memories ("RAMs"), erasable programmable read only memories ("EPROMs"), and electrically erasable programmable read only memories ("EEPROMs").

Examples of computer code that may be embodied on such computer-readable media include machine code, such as produced by a compiler, and files containing higher level code that are executed by a computer using an interpreter. For example, an embodiment of the invention may be implemented using Java, C++, or other object-oriented programming language and development tools.

While the present invention has been described with references to various specific embodiments, it should be understood by those skilled in the art that various changes may be made and equivalents substituted without departing manufactured by the spirit and scope of the invention defined by the appended claims. In addition, modifications may be made to adapt to a particular situation, material, composition of matter, method, process, series of steps to the objective of the present invention while staying within the spirit and scope of the invention and such modifications are intended to be within the scope of the appended claims. In particular, while the methods disclosed have been described with reference to particular steps in a particular order, it will be understood that these steps may be combined, sub-divided, or reordered to form an equivalent method without departing manufactured by the teachings of the present invention. Accordingly, unless specifically indicated herein, the order and grouping of steps is not a limitation of the present invention.

The invention claimed is:

1. An electronic device-implemented method for simulating a system that comprises a plurality of chemical reactions, the method comprising:

stochastically simulating the system, using the electronic device, by:

determining, using the electronic device, a reaction occurrence time for a first chemical reaction using a first probability distribution associated with the first chemical reaction, wherein the first chemical reaction is a non-mass action chemical reaction in which a reaction rate is not proportional to a product of reactant quantities of reactants involved in the non-mass action chemical reaction, and determining, using the electronic device, a reaction time for a second chemical reaction using a second probability distribution associated with the second chemical reaction; and storing the reaction occurrence time for the first chemical reaction and the reaction time for the second chemical reaction in a memory associated with the electronic device.

2. The method of claim 1, wherein the second chemical reaction is a non-mass action chemical reaction.

3. The method of claim 1, wherein the first probability distribution is different from the second probability distribution.

4. The method of claim 1, wherein the first probability distribution depends on reaction kinetics for the first chemical reaction.

5. The method of claim 4, wherein the reaction kinetics for the first chemical reaction depend on at least one environmental condition.

6. The method of claim 1, wherein the second probability distribution depends on reaction kinetics for the second chemical reaction.

7. The method of claim 6, wherein the reaction kinetics for the second chemical reaction depend on at least one environmental condition.

8. The method of claim 1, wherein the first probability distribution and the second probability distribution are defined by a user.

9. The method of claim 1, wherein the first probability distribution is automatically calculated based on kinetics of the first chemical reaction.

10. The method of claim 1, wherein the first probability distribution is derived through data collected from at least one experiment involving the first chemical reaction.

11. The method of claim 1, wherein determining a reaction time for the first chemical reaction further comprises returning, using the electronic device, a random variable from the first probability distribution.

12. The method of claim 1, wherein determining a reaction time for the second chemical reaction further comprises returning, using the electronic device, a random variable from the second probability distribution.

13. The method of claim 1, further comprising defining, using the electronic device, at least one of the first probability distribution and the second probability distribution prior to the step of determining a reaction occurrence time for a first chemical reaction.

14. The method of claim 1, wherein said first probability distribution is stored in a first reaction object containing a definition of the first chemical reaction.

15. The method of claim 14, wherein said second probability distribution is stored in a second reaction object containing a definition of the second chemical reaction.

16. The method of claim 1, wherein the probability distribution of the second reaction is impacted by the first reaction.

17. The method of claim 1, wherein the probability distribution of the second reaction is impacted by the first reaction.

18. A tangible computer-readable storage medium storing instructions for simulating a system that comprises a plurality of chemical reactions that, when executed by a processor, cause the processor to:
stochastically simulate the system by:
determining a reaction time for a first chemical reaction using a first probability distribution associated with the first chemical reaction, wherein the first chemical reaction is a non-mass action chemical reaction in which a reaction rate is not proportional to a product of reactant quantities of reactants involved in the non-mass action chemical reaction, and
determining a reaction time for a second chemical reaction using a second probability distribution associated with the second chemical reaction; and
store the reaction time for the first chemical reaction and the reaction time for the second chemical reaction in a memory.

19. The medium of claim 18, wherein the second chemical reaction is a non-mass action chemical reaction.

20. The medium of claim 18, wherein the first probability distribution is different from the second probability distribution.

21. The medium of claim 18, wherein the first probability distribution depends on reaction kinetics for the first chemical reaction.

22. The medium of claim 21, wherein the reaction kinetics for the first chemical reaction depend on at least one environmental condition.

23. The medium of claim 18, wherein the second probability distribution depends on reaction kinetics for the second chemical reaction.

24. The medium of claim 23, wherein the reaction kinetics for the second chemical reaction depend on at least one environmental condition.

25. The medium of claim 18, wherein the first probability distribution and the second probability distribution are defined by a user.

26. The medium of claim 18, wherein the first probability distribution is automatically calculated based on kinetics of the first chemical reaction.

27. The medium of claim 18, wherein the first probability distribution is derived through data collected from at least one experiment involving the first chemical reaction.

28. The medium of claim 18, wherein the step of determining a reaction time for the first chemical reaction comprises returning a random variable from the first probability distribution.

29. The medium of claim 18, wherein the step of determining a reaction time for the second chemical reaction comprises returning a random variable from the second probability distribution.

30. The medium of claim 18, further comprising the step of a user defining at least one of the first probability distribution and the second probability distribution prior to the step of determining a reaction occurrence time for a first chemical reaction.

31. The medium of claim 18, wherein said first probability distribution is stored in a first reaction object containing a definition of the first chemical reaction.

32. The medium of claim 31, wherein said second probability distribution is stored in a second reaction object containing a definition of the second chemical reaction.

* * * * *